United States Patent [19]

Matsuda et al.

[11] Patent Number: 4,931,521
[45] Date of Patent: Jun. 5, 1990

[54] OPTICAL MATERIALS COMPOSED OF RESIN FROM THIOACRYLAT ESTERS

[75] Inventors: Tatsuhito Matsuda, Kobe; Yasuaki Funae; Masahiro Yoshida, both of Suita; Tsuguo Takaya, Ohtsu, all of Japan

[73] Assignee: Nippon Shokubai Kagaku Kogyo Co., Ltd., Osaka, Japan

[21] Appl. No.: 253,340

[22] Filed: Oct. 3, 1988

Related U.S. Application Data

[62] Division of Ser. No. 138,041, Dec. 28, 1987, abandoned.

[30] Foreign Application Priority Data

Dec. 26, 1986 [JP] Japan .................................. 61-308337
Apr. 28, 1987 [JP] Japan .................................. 62-103017
Oct. 30, 1987 [JP] Japan .................................. 62-273270

[51] Int. Cl.$^5$ .............................................. C08F 20/38
[52] U.S. Cl. ...................................... 526/286; 526/289; 350/409
[58] Field of Search ................................. 526/286, 289

[56] References Cited

U.S. PATENT DOCUMENTS

| 4,536,267 | 8/1985 | Ito ................................... 204/159.23 |
| 4,654,431 | 3/1987 | DeBoer .............................. 558/257 |
| 4,745,168 | 5/1988 | Nakamoto ........................... 526/320 |
| 4,751,263 | 6/1988 | Domeier ............................. 524/513 |

FOREIGN PATENT DOCUMENTS 2093843  1/1985  United Kingdom .

Primary Examiner—Christopher Henderson
Attorney, Agent, or Firm—Sherman and Shalloway

[57] ABSTRACT

A process for producing a resin having a high refractivve index which comprises radically polymerizing a material monomer, characterized in that said material monomer comprises [I] at least one polymerizable monomer selected from the group consisting of a polyfunctional thioacrylate and a polyfnctional thiomethacrylate (as an indispensable component), and optionally [II] at least one other polymerizable monomer which is radically polymerizable with said polymerizable monomer [I], a resin having a high refractive index produced by said process and optical materials, especially lenses and disk substrates prepared from said resin.

5 Claims, No Drawings

OPTICAL MATERIALS COMPOSED OF RESIN FROM THIOACRYLAT ESTERS

This application is a division of application Ser. No. 138,041, filed Dec. 28, 1987, now abandoned.

This invention relates to a novel resin excellent in colorless transparency and having a high refractive index, a process for producing said resin and optical materials prepared from said resin.

Optical members such as lenses, prisms, optical waveguides, etc. are known in the field of the art. Materials used for producing such optical members are required to be colorless and transparent. Further, it is desirable that these materials have high refractive indices.

In the field of a lens, by using a material having a high refractive index, it becomes possible to enable a thin lens prepared from such material to have the same focal distance as that of a thick lens prepared from a material having a low refractive index. When a thin lens is used, it is possible to decrease the volume of a space occupied by a lens in optical assemblies. Thus, it brings about a merit of decreasing the weight and size of an optical apparatus in which a lens is used.

Above all, in the field of lenses for spectacles, since a resin having a high refractive index composed of a transparent synthetic resin as a material for a lens is lightweight and good in impact resistance, moldability, processability and dyeability, its applicable scope is expanding as a material for a plastic lens to take the place of an inorganic glass lens.

Heretofore, as resins used as materials for plastic lenses, diethylene glycol bisallyl carbonate resin, polymethyl methacrylate and polycarbonate have been generally used. However, since diethylene glycol bisallyl carbonate resin and polymethyl methacrylate have low refractive indices of 1.49 to 1.50, when these resins are molded into plastic lenses, the center thickness, edge thickness and curvatures of these lenses become large as compared with those of an inorganic glass lens. On the other hand, it is true that polycarbonate has a higher refractive index of 1.58 to 1.59, however, birefringence is liable to occur upon molding, and it is defective in optical homogeneity.

Further, vinyl naphthalene and vinyl carbazole give resins having high refractive indices, however, since the obtained resins have drawbacks such as being large in dispersion and remarkable in coloring, they have not been satisfactory as materials for optical plastic lenses.

Furthermore, resins prepared from polymethyl methacrylate, vinyl naphthalene and vinyl carbazole are of the non-crosslinked structures and insufficient in heat resistance, therefore, these resins fuse when they are processed like cutting or spherical grinding. So they have not been sufficient as materials in the field in which such processings are required, for example, as materials for lenses for precision optical machinery or optical elements or plastic lenses for spectacles.

Accordingly, an object of the present invention is to provide a process for producing a resin having a high refractive index which is colorless and transparent and excellent in heat resistance and low in dispersibility.

The present inventors repeated strenuous studies, finding as a result that a resin obtained by polymerizing a sulfur-containing polymerizable monomer of a specified structure in the presence of a radical polymerization initiator has a high refractive index, being colorless and transparent and excellent in heat resistance, thereby achieving the aforesaid object of the present invention.

Thus, according to the present invention, there is provided a process for producing a resin having a high refractive index, characterized by radically polymerizing material monomer or monomers comprising [I] at least one polymerizable monomer selected from the group consisting of a polyfunctional thioacrylate and a polyfunctional thiomethacrylate, and optionally [II] another polymerizable monomer which is radically polymerizable with said polymerizable monomer [I].

A polymerizable monomer [I] used in the present invention is obtained by (meth)acrylic acid esterification of thiol by a usually adopted method. For example, there may be illustrated a method of obtaining said polymerizable monomer [I] by removing hydrogen halide from thiol and a (meth)acrylic acid halide.

A polymerizable monomer [I] of the following general formulae (1), (2) and (3) which may be used in the present invention has at least one thioester group and at least two polymerizable unsaturated groups in the molecule.

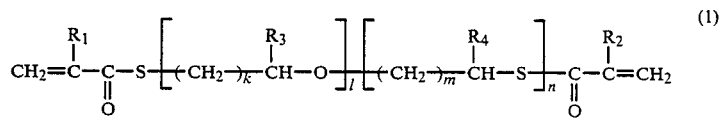
(1)

wherein $R_1$ and $R_2$ represent H or $CH_3$, $R_3$ and $R_4$ independently represents H, $CH_3$ or OH, k and m independently represent an integer of 1 to 5, and l and n independently represent 0 or an integer of 1 to 4,

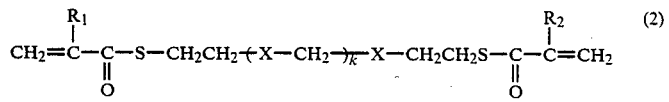
(2)

wherein $R_1$, $R_2$ and k are the same as defined in the general formula (1), and X represents O or S,

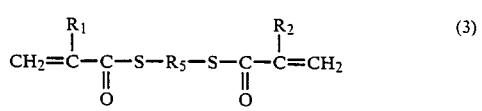
(3)

wherein $R_1$ and $R_2$ are the same as defined in the general formula (1), and $R_5$ represents a phenylene group, a xylylene group, a nucleus-substituted phenylene group or a nucleus-substituted xylylene group.

Specific examples of such monomer [I] include the following compounds. (R in the following formulae represents H or $CH_3$.)

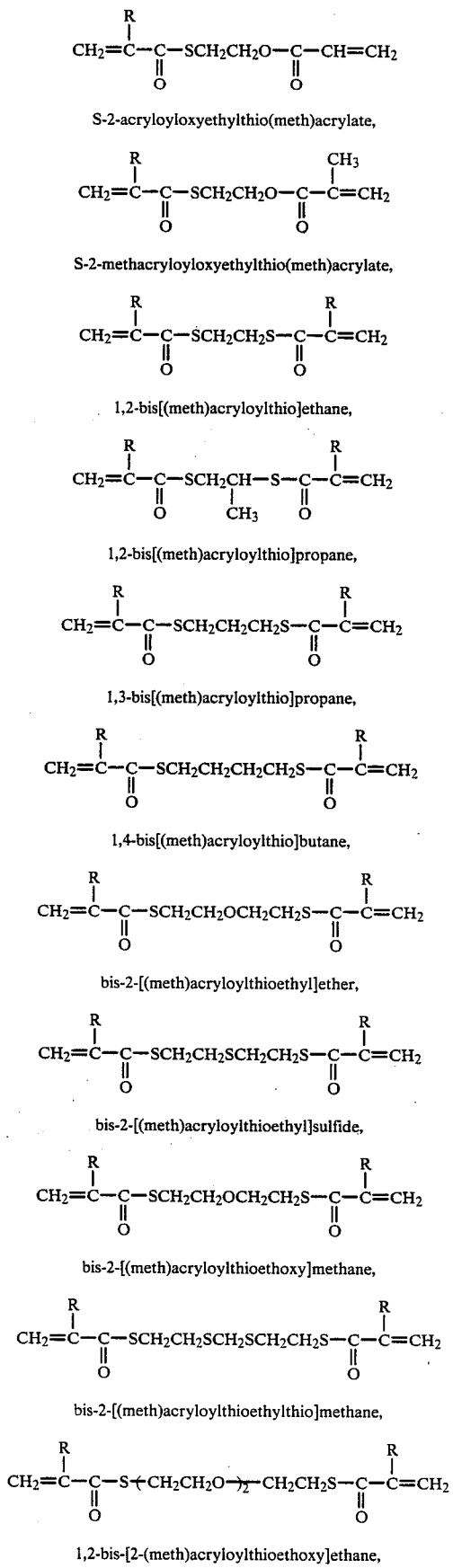
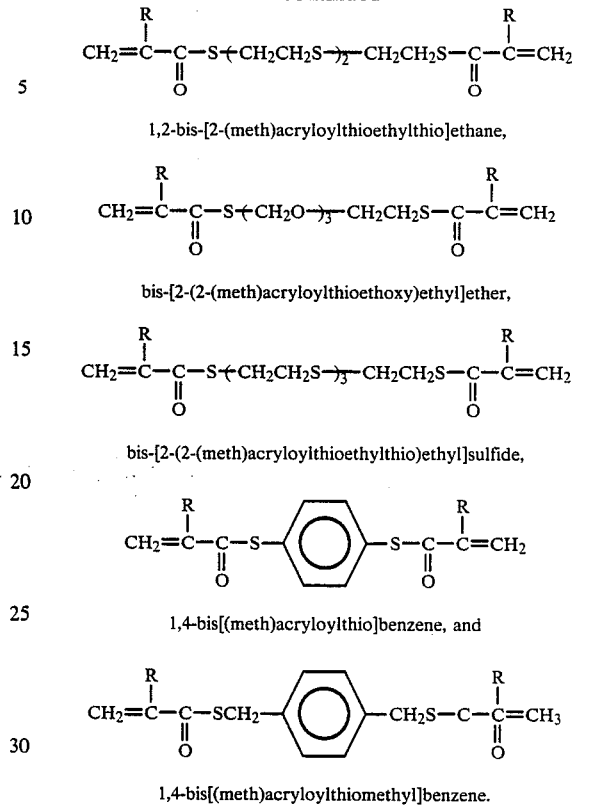

A resin having a high refractive index according to the present invention may be a polymer obtained by radically polymerizing one or more kinds of the polymerizable monomer [I] alone, but it may be a copolymer obtained by radically polymerizing optionally at least one other polymerizable monomer [II] in addition to the monomer [I].

As the other polymerizable monomer [II] which may be used in the present invention, the monomer is not particularly limited insofar as it is radically polymerizable with the polymerizable monomer [I]. For example, there may be illustrated monofunctional monomers and polyfunctional monomers not coming under the polymerizable monomer [I], polymerizable high molecular weight substances that are generally called oligomers, etc., but it is preferable that homopolymers of such monomers or oligomers have refractive indices of at least 1.48.

Specific examples of the polymerizable monomer [II] include the following compounds.

Monofunctional acrylic acid esters and methacrylic acid esters such as methyl methacrylate, butyl methacrylate, cyclohexyl methacrylate, 4-t-butylcyclohexylmethacrylate, 2,3-dibromopropyl methacrylate, phenyl acrylate, phenyl methacrylate, benzyl acrylate, benzyl methacrylate, chlorophenyl acrylate, chlorophenyl methacrylate, bromophenyl acrylate, bromophenyl methacrylate, trichlorophenyl acrylate, trichlorophenyl methacrylate, tribromophenyl acrylate, tribromophenyl methacrylate, 2-methacryloyloxymethyl thiophene, 3-methacryloyloxymethyl thiophene, 2-(2-methacryloyloxyethyl)thiophene, bromo-2-methacryloyloxymethyl thiophene, dibromo-2-methacryloyloxymethyl thiophene, tribromo-2-methacryloyloxymethyl thiophene, 2-(tricyclo[5.2.1.0$^{2,6}$]-3-decenyloxy)ethyl methacrylate, 2-(tricyclo[5.2.1.0$^{2,6}$]-3-decenylthio)ethyl methacrylate, 2-(tricyclo[5.2.1.0$^{2,6}$]-3,4-dichlorodecylthio)ethyl methacrylate and 2-(tricyclo[5.2.1.0$^{2,6}$]-3,4-dibromodecylthio)ethyl methacrylate; polyfunctional acrylic acid esters and methacrylic acid esters such as ethylene glycol dimethacrylate, propylene glycol dimethacrylate, trimethylene glycol dimethacrylate, tetramethylene glycol dimethacrylate, hexamethylene glycol dimethacrylate, diethylene glycol dimethacrylate, triethylene glycol dimethacrylate, tetraethylene glycol dimethacrylate, trimethylolpropane triacrylate, trimethylolpropane trimethacrylate, 2,2-bis-(4-acryloxyphenyl)propane, 2,2-bis-(4-methacryloyloxyphenyl)propane, 2,2-bis-(4-methacryloyloxyphenyl)propane, 2,2-bis-(4-methacryloyloxyethoxyphenyl)propane, bis-(4-methacryloyloxyethoxyphenyl)sulfone, 2,2-bis-(3,5-dibromo-4-methacryloyloxyethoxyphenyl)propane, 2,5-bismethacryloyloxymethylthiophene and 2,5-bismethacryloyloxymethyl- 3,4-dibromothiophene; 2-halogenoacrylic acid esters such as methyl-2-chloroacrylate, methyl-2-bromoacrylate, cyclohexyl-2-chloroacrylate, cyclohexyl-2-bromoacrylate, 2-(tricyclo[5.2.1.0$^{2,6}$]-3-decenyloxy)ethyl-2-chloroacrylate, 2-(tricyclo[5.2.1.0$^{2,6}$]-3-decenylthio)ethyl-2-chloroacrylate and 2-(tricyclo[5.2.1.0$^{2,6}$]-3,4-dibromodecylthio)ethyl-2-chloroacrylate; thioacrylic acid esters and thiomethacrylic acid esters such as methyl thioacrylate, methyl thiomethacrylate, butyl thioacrylate, butyl thiomethacrylate, phenyl thioacrylate, phenyl thiomethacrylate, benzyl thioacrylate and benzyl thiomethacrylate; unsaturated nitriles such as acrylonitrile and methacrylonitrile; allyl esters, allyl carbonate and allyl ethers such as allyl benzoate, diallyl phthalate, diethylene glycol bisallyl carbonate, 2,2-bis-(4-allyloxycarbonyloxyethoxy-3,5-dibromophenyl)propane and 2,2-bis-(4-allyloxy-3,5-dibromophenyl)propane; vinyl aromatic groups such as styrene, chlorostyrene, bromostyrene, dichlorostyrene, dibromostyrene, methyl styrene and divinyl benzene; and reactive oligomers such as epoxy acrylate, epoxy methacrylate, polyester acrylte, polyester methacrylate, polyurethane acrylate and polyurethane methacrylate.

In the present invention, the polymerizable monomer [I] imparts a high refractive index and a cross-linked structure to a polymer. Hence, it is of use to give a resin having a high refractive index, being excellent in heat resistance, unlikely to be fused or blocked upon being subjected to processing such as cutting and spherical grinding and not adhering to processing tools. In order to have such characteristics sufficiently develop, it is preferable to use the polymerizable monomer [I] in an amount of at least 5% by weight, especially at least 10% by weight based on the entire material monomer(s). When the monomer [I] is used in an amount of less than 5% by weight, the contribution of the monomer [I] to elevation of the refractive index becomes small, the cross-linking density becomes small and the effect of advancing the heat resistance, cutting processability and spherical grinding processability by the monomer [I] becomes small.

The kind and amount of the polymerizable monomer [II] optionally used in the present invention are properly selected by taking into consideration the refractive index of a resin having a high refractive index to be obtained. To obtain a resin having a high refractive index and being excellent in colorless transparency, it is suitable that the amount of said monomer [II] is less than 95% by weight, especially less than 90% by weight based on the entire material monomer(s).

The resin having a high refractive index according to the present invention is produced by radically polymerizing the material monomer containing the polymerizable monomer [I] as an indispensable component and optionally containing the polymerizable monomer [II].

The method of radical polymerization is not particularly limited and conventional and known methods may be adopted. As specific examples of said method, for example, the following methods may be illustrated.

(1) A method of heat polymerizing the material monomer in the presence of a radical polymerization initiator.

(2) A method of ultraviolet ray polymerization of the material monomer in the presence of a photosensitizer.

(3) A method of electron beam polymerization of the material monomer.

The method of (1) is a most general method, in which an apparatus is simple and a radical polymerization initiator is relatively cheap.

When the method of (2) is adopted, a curing speed is fast and it is possible to shorten the polymerization time.

The method of (3) enables the material monomer to be polymerized in the absence of a radical polymerization initiator or a photosensitizer. Therefore, according to this method, it is possible to prevent impurities from mixing in a resin having a high refractive index to some extent.

In the case of carrying out the polymerization according to the method (1), the actual methods of polymerization are not particularly limited, but conventional and known methods may be adopted, for example, bulk polymerization (especially casting polymerization), solution polymerization, suspension polymerization and emulsion polymerization may be illustrated. Of these modes, casting polymerization is capable of shaping a polymer formed by polymerization in a mold into a desired shape. Hence, it is particularly preferable. It is possible to adopt a method of, for example, casting the material monomer added with a radical polymerization initiator into a glass mold and gradually elevating the temperature from around 30° to 60° C. to a higher temperature, thereby polymerizing the material monomer. And by properly selecting the kind and using amount of the polymerization initiator, it is possible to shape the obtained polymer into a resin having a high refractive index by a reaction injection method (RIM) also. When a method other than the casting polymerization is adopted within the framework of bulk polymerization, however, a step of shaping the obtained polymer into a desired shape is required.

As a radical polymerization initiator which may be used upon carrying out a polymerization, there may be illustrated, for example, a peroxide such as benzoyl peroxide, acetyl peroxide, di-t-butyl peroxide, diisopropyl peroxy dicarbonate and t-butyl peroxy-2-ethylhexanoate and azo compounds such as 2,2'-azobisisobutyronitrile, 2,2'-azobis(2,4-azobis(2,4-dimethylvaleronitrile) and 1,1'-azobis(cyclohexane-1-carbonitrile). These initiators may be used singly or in combination in an amount of usually 0.01 to 10% by weight, preferably 0.05 to 5% by weight based on the material monomer and in combination with a promoter as required.

Since the polymerization conditions are influenced by the kind and composition of the material monomer and the kind of the polymerization initiator, they may not be limited without reserve, however, generally, polymerization conditions of initiating a polymerization at a relatively low temperature, slowly elevating the temperature and carrying out a post-polymerization at a high temperature upon completion of the polymerization to cure the obtained polymer are suitable.

And since a polymerization time differs in accordance with various conditions, it is suitable to decide the optimum polymerization time in accordance with these various conditions in advance, but generally it is preferable to select these conditions so that the polymerization may be completed within 2 to 40 hours.

In the methods of (2) and (3), it is usually suitable to adopt casting polymerization, however, in the method of (2), the use of a photosensitizer is required. For example, in the method of (2), by irradiating ultraviolet rays to the material monomer blended with a photosensitizer, and in the method of (3), by irradiating an electron beam to the material monomer per se, it is possible to easily obtain a resin having a high refractive index, respectively.

As a photosensitizer which may be used in the method of (2), there may be illustrated, for example, benzoin, benzoin methyl ether, benzoin ethyl ether, benzoin isopropyl ether, benzoin butyl ether, 2-hydroxy-2-benzoyl propane, benzyl dimethyl ketal, azobisisobutyronitrile and thioxanthone. They may be used singly or in combination in an amount of usually 0.01 to 10% by weight, preferably 0.05 to 8% by weight based on the material monomer.

In the present invention, which of the polymerization methods (1) to (3) should be adopted may be properly selected in accordance with the desired performance of a resin having a high refractive index, and as required a plurality of these methods may be combined.

A resin having a high refractive index produced by the process of the present invention may properly contain known additives, for example, a ultraviolet absorber, an antioxidant, a drip inhibitor and a coloring agent.

A resin having a high refractive index produced by the process of the present invention may be obtained by the use of the polymerizable monomer [I] as an indispensable component, therefore, it has a high refractive index, in addition, it is excellent in colorless transparency, heat resistance and cutting processability.

Accordingly, it may be used as a resin for optical materials, for example, as members of lenses, prisms, optical waveguides, optical disks and films. Besides, by blending a pigment and fillers with said resin, the blends may be used as shaped articles for decoration and building materials as well.

Hereinbelow, the present invention will be specifically explained by way of examples.

For information, methods of evaluating the physical properties in each example are as follows.

[COLORLESS TRANSPARENCY]

The degree of coloration of a 1.5 mm-thick sheet-like polymer obtained by casting polymerization was adjudicated by visual observation with the naked eyes.

[REFRACTIVE INDEX AND ABBE NUMBER]

A small piece of a 1.5 mm-thick sheet-like polymer obtained by casting polymerization was measured of a refractive index using an Abbe's refractometer, and Abbe number was sought from a dispersion table.

[ENTIRE LIGHT TRANSMISSION]

A 1.5 mm-thick sheet-like polymer obtained by casting polymerization was measured of the transmission using a hazemeter.

[CUTTING PROCESSABILITY]

A 1.5 mm-thick sheet-like polymer obtained by casting polymerization was cut with a diamond cutter, and crack, fissure and fusion, if any, of a cut surface arising as a result were observed. A polymer whose cut surface was entirely free from crack, fissure and fusion was indicated as a mark ○.

[HEAT RESISTANCE]

A 1.5 mm-thick sheet-like polymer obtained by casting polymerization was placed in a hot air dryer at 100° C. for 3 hours and deformation of the polymer such as warping, if any was observed. The polymer sheet of which no deformation was observed at all was indicated by a mark ○.

[PENCIL HARDNESS]

It was measured in accordance with JIS K5400.

[IMPACT RESISTANCE (OF A LENS)]

It was evaluated in accordance with ASTM F659. Namely, onto a lens having a center thickness of 2.0 mm, a steel ball having a weight of 16.2 g was dropped from the height of 127 cm, and the lens that was not broken was indicated by a mark ○.

[IMPACT RESISTANCE (OF A DISK)]

Onto a disk having a thickness of 1.5 mm, a steel ball having a weight of 16.2 g was dropped from the height of 100 cm, and a disk that was not broken was indicated by a mark , a disk that was fissured by a mark Δ, and a disk that was broken by a mark X.

[DYEABILITY]

In a hot water (at more than 85° C.) dissolving a dispersed dye (dispersed brown), a lens was immersed for 10 minutes and the dyed state of the lens was observed, and a lens that could be dyed without a color shade was indicated by a mark ○.

[APPEARANCE]

The hue, transparency and optical surface state were visually observed with the naked eyes, and the polymer sheet which was colorless, transparent and good in surface state was indicated as "good".

[HYGROSCOPICITY]

Water absorption was measured in accordance with JIS K7209 and indicated by the value obtained.

[WARPING]

The center of a disk was supported by a support having a diameter of 30 mm, the disk was retained at 60° C. for 5 hours and the warping of the disk at that time was measured.

The meanings of the abbreviations used in the following Tables 1 to 5 are as follows.

| AN | acrylonitrile |
|---|---|
| ADC | diethylene glycol bisallyl carbonate |
| AIBN | 2,2'-azobis (isobutyronitrile) |

-continued

| | |
|---|---|
| BMTE | 1,2-(bismethacryloylthio)ethane |
| BMTEE | bis(2-methacryloylothioethyl)ether |
| BMTES | bis(2-methacryloylthioethyl)sulfide |
| BMTEEE | 1,2-bis(2-methacryloylthioethoxy)ethane |
| BMTEM | bis(2-methacryloylthioethoxy)methane |
| BMTMB | 1,4-bis(methacryloylthiomethyl)benzene |
| BzMA | benzyl methacrylate |
| Br$_4$BMEPP | 2,2-bis(3,5-dibromo-4-methacryloyloxy-ethoxyphenyl)propane |
| ClSt | p-chlorostyrene |
| DTEMA | 2-(tricyclo[5.2.1.0$^{2,6}$]-3-decenyl-thio)ethyl methacrylate |
| HMPBT | 2-(2-hydroxy-5-methylphenyl)benzotriazole |
| IPP | diisopropylperoxy dicarbonate |
| MAN | methacrylonitrile |
| MMA | methyl methacrylate |
| MTMA | S-methyl thiomethacrylate |
| MMP | 4-methacryloyloxy-2,2,6,6-tetramethyl piperidine |
| MCA | methyl-2-chloroacrylate |
| St | styrene |
| SBzTMA | S-benzyl thiomethacrylate |
| TBPMA | 2,4,6-tribromophenyl methacrylate |
| TeEDMA | tetraethylene glycol dimethacrylate |
| TMMA | 2-methacryloyloxymethyl thiophene |
| V-65 | 2,2'-azobis(2,4-dimethylvaleronitrile) |
| V-40 | 1,1'-azobis(cyclohexane-1-carbonitrile) |

EXAMPLE 1

A mixture of 100 parts by weight of 1,2-bis(methacryloylthio)ethane and 0.5 part by weight of 2,2'-azobis(2,4-dimethylvaleronitrile) was cast into a mold consisting of 2 glass plates and a silicone rubber gasket, and heated at 50° C. for 6 hours, at 60° C. for 16 hours and at 90° C. for 2 hours to polymerize the monomeric mixture. The obtained resin having a high refractive index [1] was colorless and transparent. The various physical properties of this resin are shown in Table 1.

EXAMPLE 2

A mixture of 70 parts by weight of 1,2-bis(methacryloylthio)ethane, 20 parst by weight of styrene, 10 parts by weight of benzyl methacrylate, 0.2 part by weight of 2-(2-hydroxy-5-methylphenyl)benzotriazole and 0.5 part by weight of 2,2'-azobis(2,4-dimethylvaleronitrile) was cast into a mold consisting of 2 glass plates and a silicone rubber gasket, and was heated at 50° C. for 6 hours, at 60° C. for 16 hours and further at 90° C. for 2 hours to polymerize the monomeric mixture. The obtained resin having a high refractive index [2] was colorless and transparent. The various physical properties of this resin are shown in Table 1.

EXAMPLES 3 to 7

Example 2 was repeated except that the composition of the material monomer was changed as shown in Table 1 to obtain resins having high refractive indices [3] to [7]. The various physical properties of these resins [3] to [7] are also shown in Table 1.

COMPARATIVE EXAMPLE 1

A mixture of 100 parts by weight of diethylene glycol bisallyl carbonate and 25 parts by weight of diisopropyl peroxy dicarbonate was cast into a mold consisting of 2 glass plates and a silicone rubber gasket, and was heated at 40° C. for 1 hour, at 45° C. for 1 hour, at 50° C. for 1 hour, at 60° C. for 16 hours, at 90° C. for 2 hours, and further at 110° C. for 2 hours to polymerize the mixture. The obtained resin for comparison [1] was colorless and transparent. The various physical properties of the resin for comparison (1) are also shown in Table 1.

COMPARATIVE EXAMPLE 2

A mixture of 100 parts by weight of methyl methacrylate and 0.5 part by weight of 2,2-azobis(2,4-dimethylvaleronitrile) was cast into a mold consisting of 2 glass plates and a silicone rubber gasket, and was heated at 50° C. for 6 hours, at 60° C. for 16 hours, and further at 90° C. for 2 hours to polymerize the mixture. The obtained resin for comparison [2] was colorless and transparent. The various physical properties of this resin for comparison [2] are also shown in Table 1.

TABLE 1

| Example | Material monomer Polymerizable monomer [I] (parts by weight) | Material monomer Polymerizable monomer [II] (parts by weight) | Polymerization initiator (parts by weight) | Additive (parts by weight) | Appearance | Refractive index | Abbe number | Entire light transmission (%) | Cutting processability | Heat-resistance |
|---|---|---|---|---|---|---|---|---|---|---|
| 1 | BMTE (100) | — | V-65 (0.5) | — | Colorless transparent | 1.608 | 34.5 | 92 | O | O |
| 2 | BMTE (70) | St (20) BzMA (10) | V-65 (0.2) | HMPBT (0.2) | Colorless transparent | 1.601 | 34.0 | 91 | O | O |
| 3 | BMTE (60) | BzMA (20) TBPMA (20) | V-65 (0.2) | HMPBT (0.2) | Colorless transparent | 1.609 | 32.8 | 90 | O | O |
| 4 | BMTE (60) | BzMA (20) TBPMA (20) | V-65 (0.2) | HMPBT (0.2) | Colorless transparent | 1.604 | 34.0 | 91 | O | O |
| 5 | BMTE (50) | BzMA (20) Br$_4$BMEPP (30) | V-65 (0.2) | HMPBT (0.2) | Colorless transparent | 1.595 | 32.9 | 91 | O | O |
| 6 | BMTEE (60) | BzMA (20) TBPMA (20) | V-65 (0.2) | HMPBT (0.2) | Colorless transparent | 1.595 | 35.3 | 91 | O | O |
| 7 | BMTEE (50) | BzMA (20) Br$_4$BMEPP (30) | V-65 (0.2) | HMPBT (0.2) | Colorless trans- | 1.588 | 34.0 | 90 | O | O |

TABLE 1-continued

| Example | Material monomer Polymerizable monomer [I] (parts by weight) | Polymerizable monomer [II] (parts by weight) | Polymerization initiator (parts by weight) | Additive (parts by weight) | Appearance | Refractive index | Abbe number | Entire light transmission (%) | Cutting processability | Heat resistance |
|---|---|---|---|---|---|---|---|---|---|---|
| Comparative Example 1 | — | ADC (100) | IPP (2.5) | — | Colorless transparent | 1.500 | 58.8 | 92 | O | O |
| Comparative Example 2 | — | MMA (100) | V-65 (0.5) | — | Colorless transparent | 1.491 | 57.8 | 92 | Fused | Deformed |

EXAMPLE 8

A mixture of 50 parts by weight of bis(2-methacryloylthioethyl)sulfide, 40 parts by weight of styrene, 10 parts by weight of acrylonitile, 0.1 part by weight of 2-(2-hydroxy-5-methylphenyl)benzotriazole, 0.1 part by weight of 4-methacryloyloxy-2,2,6,6-tetramethyl piperidine and 0.5 part by weight of 2,2'-azobis(2,4-dimethylvaleronitrile) was cast into a mold consisting of 2 glass plates and a silicone rubber gasket, and was heated at 50° C. for 6 hours, at 60° C. for 16 hours and further at 110° C. for 2 hours to polymerize the monomeric mixture. The obtained resin having a high refractive index [8] was colorless and transparent. The various physical properties of this resin having a high refractive index are shown in Table 2.

EXAMPLES 9 to 15

Example 8 was repeated except that the composition of the material monomer was changed as shown in Table 2 to obtain resins having high refractive indices [9] to [15]. The various physical properties of these resins [9] to [15] are also shown in Table 2.

TABLE 2

| Example | Material monomer Polymerizable monomer [I] (parts by weight) | Polymerizable monomer [II] (parts by weight) | Polymerization initiator (parts by weight) | Additive (parts by weight) | Appearance | Refractive index | Abbe number | Entire light transmission (%) | Cutting processability | Heat resistance |
|---|---|---|---|---|---|---|---|---|---|---|
| 8 | BMTES (50) | St (40) AN (10) | V-65 (0.5) | HMPBT (0.1) MMP (0.1) | Colorless transparent | 1.596 | 33.6 | 91 | O | O |
| 9 | BMTEE (50) | St (40) AN (10) | V-65 (0.5) | HMPBT (0.1) MMP (0.1) | Colorless transparent | 1.585 | 33.7 | 91 | O | O |
| 10 | BMTEEE (50) | St (40) AN (10) | V-65 (0.5) | HMPBT (0.1) MMP (0.1) | Colorless transparent | 1.573 | 35.2 | 90 | O | O |
| 11 | BMTES (30) | SBzTMA (50) St (10) AN (10) | V-65 (0.5) | HMPBT (0.1) MMP (0.1) | Colorless transparent | 1.608 | 32.8 | 90 | O | O |
| 12 | BMTES (50) | DTEMA (50) | V-65 (0.5) | HMPBT (0.2) | Colorless transparent | 1.587 | 42.0 | 90 | O | O |
| 13 | BMTEEE (50) | St (30) MCA (20) | V-65 (0.5) | HMPBT (0.2) | Colorless transparent | 1.565 | 40.5 | 90 | O | O |
| 14 | BMTEEE (50) | St (30) TMMA (20) | V-65 (0.5) | HMPBT (0.2) | Colorless transparent | 1.578 | 36.5 | 91 | O | O |
| 15 | BMTEEE (50) | St (30) MTMA (20) | V-65 (0.5) | HMPBT (0.2) | Colorless transparent | 1.578 | 36.5 | 91 | O | O |

EXAMPLE 16

A mixture of 40 parts by weight of bis(2-methacryloylthioethoxy)methane, 40 parts by weight of styrene, 20 parts by weight of benzyl methacrylate, 0.2 part by weight of 2-(2-hydroxy-5-methylphenyl)benzotriazole, 0.2 part by weight of 2,2'-azobis(2,4-dimethylvaleronitrile) and 0.1 part by weight of 1,1'-azobis(cyclohexane-1-carbonitrile) was cast into a mold consisting of 2 glass plates and a silicone rubber gasket, and was heated at 50° C. for 6 hours, at 60° C. for 16 hours, and further at 110° C. for 2 hours to polymerize the monomeric mixture.

The obtained resin having a high refractive index [16] was colorless and transparent. The various physical properties of this resin [16] are shown in Table 3.

EXAMPLES 17 to 18

Example 16 was repeated except that the composition of the material monomer was changed as shown in Table 3 to obtain resins having high refractive indices [17] and [18]. The various physical properties of these resins [17] and [18] having high refractive indices are also shown in Table 3.

EXAMPLE 19

A mixture of 50 parts by weight of bis(2-methacryloylthioethyl)sulfide, 40 parts by weight of styrene, 10 parts by weight of acrylonitrile and 2.0 parts by weight of benzoin isopropylether was cast into a mold consisting of 2 glass plates and a silicone rubber gasket, to both surfaces of the content, ultraviolet rays were irradiated from a distance of 10 cm for total 120 seconds, respectively using a 3 KW high-pressure mercury lamp having a lamp output of 80 W/cm and then the content was heated at 110° C. for 2 hours to be polymerized. The obtained resin having a high refractive index [19] was colorless and transparent. The various physical properties of this resin [19] are also shown in Table 3.

EXAMPLE 20

A material monomer consisting of 55 parts by weight of bis(2-methacryloylthioethyl)sulfide, 30 parts by weight of styrene, 15 parts by weight of acrylonitile, 0.1 part by weight of 2-(2-hydroxy-5-methylphenyl)benzotriazole and 0.1 part by weight of 4-methacryloyloxy-2,2,6,6-tetramethyl piperidine was added with 0.1 part by weight of 2,2'-azobis(2,4-dimethylvaleronitrile) and 0.1 part by weight of 1,1'-azobis(cyclohexane-1-carbonitrile), and the resulting mixture was cast into a space produced by a glass mold having an internal diameter of 75 mm so designed as to give a lens having a diopter of −3.00 D and an ethylene/vinyl acetate copolymer gasket so designed as to make the center thickness 2.0 mm.

The content of the space was retained in a constant temperature vessel at 60° C. for 6 hours, then the gasket was removed and the temperature was gradually elevated at 110° C. over 8 hours, and further retained at 110° C. for 2 hours to thereby effect a casting polymerization. Then, the glass mold was released from the resulting polymer to thereby give a lens [1] having a diameter of 75 mm and a diopter of −3.00 D. The optical surface state of the obtained lens [1] was good and its various physical properties as a lens were excellent as shown in Table 4.

EXAMPLES 21 to 24

Example 20 was repeated except that the composition of the mixture consisting of the material monomer and the polymerization initiators were changed as shown in Table 4 to give lenses [2] to [5]. The various physical properties of these as lenses were excellent as shown in Table 4.

TABLE 3

| Example | Material monomer Polymerizable monomer [I] (parts by weight) | Material monomer Polymerizable monomer [II] (parts by weight) | Polymerization initiator (parts by weight) | Additive (parts by weight) | Appearance | Refractive index | Abbe number | Entire light transmission (%) | Cutting processability | Heat resistance |
|---|---|---|---|---|---|---|---|---|---|---|
| 16 | BMTEM (40) | St (40) BzMA (20) | V-65 (0.2) V-40 (0.1) | HMPBT (0.2) | Colorless transparent | 1.586 | 34.8 | 91 | O | O |
| 17 | BMTMB (30) | St (30) BzMA (30) TeEDMA (10) | V-65 (0.2) V-40 (0.1) | HMBPT (0.2) | Colorless transparent | 1.584 | 35.2 | 90 | O | O |
| 18 | BMTES (50) BMTEEE (30) | St (20) | V-65 (0.2) V-40 (0.1) | HMPBT (0.2) | Colorless transparent | 1.597 | 36.4 | 90 | O | O |
| 19 | BMTES (50) | St (40) AN (10) | Benzoin isopropylether (2.0) | — | Colorless transparent | 1.596 | 33.6 | 91 | O | O |

TABLE 4

| Example | Material monomer Polymerizable monomer [I] (parts by weight) | Material monomer Polymerizable monomer [II] (parts by weight) | Polymerization initiator (parts by weight) | Additive (parts by weight) | Appearance | Dioper |
|---|---|---|---|---|---|---|
| 20 | BMTES (55) | St (30) AN (15) | V-65 (0.1) V-40 (0.1) | HMPBT (0.1) MMP (0.1) | Good | −3.00D |
| 21 | BMTEEE (30) | SBzTMA (50) St (10) MAN (10) | V-65 (0.2) V-40 (0.1) | HMPBT (0.1) MMP (0.1) | " | −3.00D |
| 22 | BMTEEE (40) BMTES (15) | ClSt (25) MAN (20) | V-65 (0.2) V-40 (0.1) | HMPBT (0.1) MMP (0.1) | " | −4.50D |
| 23 | BMTES (50) | St (35) AN (10) ADC (5) | V-65 (0.2) V-40 (0.1) | HMPBT (0.1) MMP (0.1) | " | −3.00D |
| 24 | BMTES (50) | ClSt (20) St (15) AN (15) | V-65 (0.2) V-40 (0.1) | HMPBT (0.1) MMP (0.1) | " | −3.00D |

Refractive  Pencil  Cutting  Heat-  Impact

TABLE 4-continued

| Example | index/Abbe number | hardness | processability | resistance | resistance | Dyeability |
|---|---|---|---|---|---|---|
| 20 | 1.597/35.2 | 4H | O | O | O | O |
| 21 | 1.594/34.8 | 4H | O | O | O | O |
| 22 | 1.577/37.2 | 4H | O | O | O | O |
| 23 | 1.592/36.3 | 3H | O | O | O | O |
| 24 | 1.597/35.7 | 4H | O | O | O | O |

EXAMPLE 25

A material monomer consisting of 50 parts by weight of bis(2-methacryloylthioethyl)sulfide, 40 parts by weight of styrene, 10 parts by weight of acrylonitile, 0.1 part by weight of 2-(2-hydroxy-5-methylphenyl)benzotriazole and 0.1 part by weight of 4-methacryloyloxy-2,2,6,6-tetramethyl piperidine was added with 0.5 part by weight of 2,2'-azobis(2,4-dimethylvaleronitrile), and the resulting mixture was cast into a mold consisting of 2 glass plates and a silicone rubber gasket, and was heated at 50° C. for 6 hours, at 60° C. for 16 hours, and further at 110° C. for 2 hours to thereby effect a casting polymerization. Then, the polymerization product was removed from the mold to thereby give a disk substrate [1] having a thickness of 1.5 mm and a diameter of 30 cm. The obtained disk substrate [1] was colorless and transparent and its various physical properties required as a disk substrate such as warping, hygroscopicity and impact resistance were excellent as shown in Table 5.

EXAMPLES 26 AND 27 AND COMPARATIVE EXAMPLES 3 AND 4

Example 25 was repeated except that the composition of the mixture consisting of the material monomer and additives was changed as shown in Table 5 to give disk substrates [2] and [3] as well as disk substances [1] and [2] for comparison. The various physical properties of these as disk substrates are shown in Table 5. As will be seen from said table, the disk substrates composed of the resins having high refractive indices of the present invention were excellent. In contrast, the disk substrates for comparison were inferior in each physical properties of hardness, heat resistance, impact resistance, hygroscopicity and warping.

TABLE 5

| Example | Material monomer Polymerizable monomer [I] (parts by weight) | Material monomer Polymerizable monomer [II] (parts by weight) | Polymerization initiator (parts by weight) | Additive (parts by weight) | Appearance | Refractive index/Abb Entire light transmission |
|---|---|---|---|---|---|---|
| 25 | BMTES (50) | St (40) AN (10) | V-65 (0.5) | HMPBT (0.1) MMP (0.1) | Colorless transparent | 1.596/33.6 91 |
| 26 | BMTES (30) | SBzTMA (50) St (10) AN (10) | V-65 (0.5) | HMPBT (0.1) MMP (0.1) | Colorless transparent | 1.608/32.8 90 |
| 27 | BMTEEE (50) | St (30) MTMA (20) | V-65 (0.5) | HMPBT (0.2) | Colorless transparent | 1.578/36.5 91 |
| Comparative Example 3 | — | MMA (100) | AIBN (0.5) | HMPBT (0.2) | Colorless | 1.492/49.7 91 |
| Comparative Example 4 | — | St (80) AN (20) | V-65 (0.5) | HMPBT (0.2) | Colorless transparent | 1.577/33.4 91 |

| Example | Pencil hardness | Heat resistance | Impact resistance | Hygroscopicity | Warping |
|---|---|---|---|---|---|
| 25 | 4H | O | O | 0.18 | Almost none |
| 26 | 4H | O | O | 0.13 | Almost none |
| 27 | 4H | O | Δ | 0.21 | Almost none |
| Comparative Example 3 | 2H | Δ | X | 0.30 | Warped by 3–5 mm |
| Comparative Example 4 | H | Δ | X | 0.20 | Warped by 1–2 mm |

What we claim is:

1. An optical material prepared from a resin having a high refractive index produced by radically polymerizing a material monomer, said material monomer comprising:

[I] at least one polymerizable polyfunctional thioacrylate or polyfunctional thiomethacrylate represented by the general formula (1)

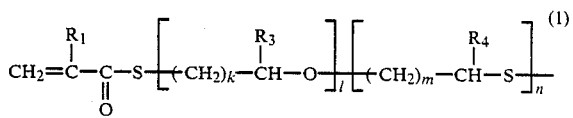

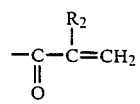

wherein $R_1$ and $R_2$ represent H or $CH_3$, $R_3$ and $R_4$ independently represent H, $CH_3$ or OH, k and m independently represent an integer of 1 to 5, and 1 and n independently represent 0 or an integer of 1 to 4, the general formula (2)

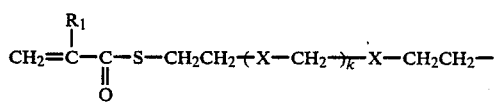

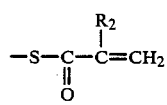

wherein $R_1$, $R_2$ and k are the same as defined in the general formula (1), and X represents O or S, or the general formula (3)

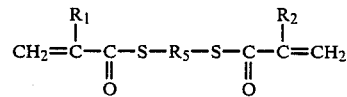

wherein $R_1$ and $R_2$ are the same as defined in the general formula (1), and $R_5$ represents a phenylene group, a xylylene group, a nucleus-substituted phenylene group or a nucleus-substituted xylylene group; and optionally [II] at least one other polymerizable monomer which is radically polymerizable with said polymerizable monomer [I].

2. The optical material according to claim 1, wherein the content of said polymerizable monomer [I] is at least 5% by weight based on said material monomer.

3. The optical material according to claim 1, wherein the content of said polymerizable monomer [I] is at least 10% by weight based on said material monomer.

4. The optical material according to claim 1, wherein as said polymerizable monomer [II], a monomer whose homopolymer has a refractive index of at least 1.48 is used.

5. The optical material according to claim 1, which has a refractive index of at least 1.55.

* * * * *